United States Patent [19]

Sawa et al.

[11] Patent Number: 4,596,868
[45] Date of Patent: Jun. 24, 1986

[54] PROCESS FOR SYNTHESIZING 2-VINYL-4,6-DIAMINO-S-TRIAZINE

[75] Inventors: Natsuo Sawa, Tadotsu; Takeshi Masuda, Marugame, both of Japan

[73] Assignee: Shikoku Chemicals Corporation, Kagawa, Japan

[21] Appl. No.: 768,639

[22] Filed: Aug. 23, 1985

[51] Int. Cl.$^4$ .......................................... C07D 251/18
[52] U.S. Cl. ................................................ 544/205
[58] Field of Search ........................................ 544/205

[56] References Cited

U.S. PATENT DOCUMENTS 2,381,121  8/1945  Ericks ................................. 544/205
4,113,947  9/1978  Deiner et al. ....................... 544/205

Primary Examiner—John M. Ford
Attorney, Agent, or Firm—Sherman and Shalloway

[57] ABSTRACT

2-Vinyl-4,6-diamino-s-triazine is synthesized in a high yield by reacting 2-(2'-methylimidazolyl-(1'))-ethyl-4,6-diamino-s-triazine with epichlorohydrin. The reaction may be carried out in an aqueous medium in the presence of a catalytic amount of a polymerization inhibitor.

6 Claims, No Drawings

PROCESS FOR SYNTHESIZING 2-VINYL-4,6-DIAMINO-S-TRIAZINE

BACKGROUND OF THE INVENTION

1. Field of the Invention

This invention relates to a process for synthesizing 2-vinyl-4,6-diamino-s-trazine (to be abbreviated as VT).

2. Description of the Prior Art

VT is a compound represented by the following structural formula, and has vinyl-polymerizability.

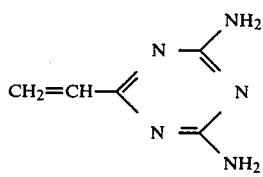

VT has a melting point of 239° to 241° C., and is soluble in hot water but sparingly soluble in hot methanol, hot ethanol and hot acetone. It is almost neutral. When VT is dissolved in hot water and azobisisobutyronitrile is added, a polymer insoluble in hot water is formed.

TLC (alumina and silica, EtOH): Rf=0.0

$v_{cm-1}{}^{KBr}$: 3340, 3170, 1680 (4th absorption), 1655 (2nd absorption), 1550 (1st absorption), 1460 (5th absorption), 1425 (3rd absorption), 1370, 1265, 1130, 985, 960, 835 (6th absorption).

NMR (d$_6$-DMSO): δ 6.76 (m, 4H), 6.35–6.45 (t, 2H), 5.59–5.72 (q, 1H).

Elementary analysis: C 44.28%, H 5.07%, N 50.02%.

VT is useful as a comonomer. It is known that when diamino-s-triazine-group is introduced into a side chain of a polymer, the softening point and glass transition point of the polymer become much higher than the original polymer, its specific gravity also increases, and its solubility changes remarkably (see, for example, Seo and Kakurai: Collection of Papers on Polymers (the Japanese-language publication), 32, 308 (1975); T. Seo, K. Abe, H. Honma, T. Kakurai: Polym. Prepn., 20, 661 (1979)).

Various methods have already been known for the synthesis of VT. They include, for example, the reaction of biguanide with acryloyl chloride (C. G. Overberger et al.: J. A. C. S., 80, 988 (1958)), the reaction of dicyandiamide with β-dimethylamino-propionitrile (Hoechst, French Pat. No. 1,563,255 (1967)), the heating of 1,2-di(4',6'-diamino-s-striazinyl-(2)')-cyclobutane to 320° C. under reduced pressure (Asahi Chemical Industry, Co., Ltd.: Japanese Patent Publication No. 35068/1971), and the heating of 2-β-methoxyethyl-4,6-diamino-s-triazine to 350° C. in a stream of nitrogen (Suddeutsche Kalkstickstoff Werke A.G.: German OLS No. 2,135,881 (1973)).

None of these prior methods for the synthesis of VT, however, lend themselves to industrial-scale practice for one or more reasons. For example, the starting materials are expensive, the reaction operation is complex, or the yield of VT is low.

SUMMARY OF THE INVENTION

The present inventors have now found that VT can be obtained in a high yield by reacting 2-(2'-methylimidazolyl-(1'))-ethyl-4,6-diamino-s-triazine (to be abbreviated as 2MA) with epichlorohydrin at an elevated temperature in an aqueous medium.

This reaction is schematicaly shown as follows:

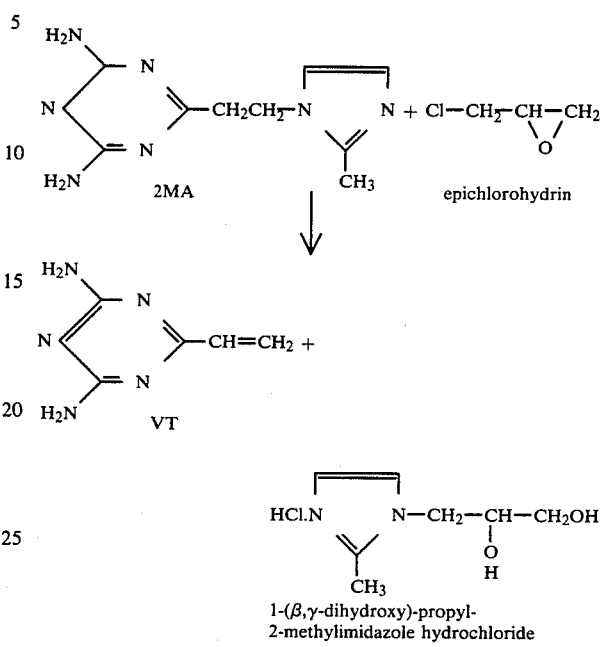

1-(β,γ-dihydroxy)-propyl-2-methylimidazole hydrochloride

DETAILED DESCRIPTION OF PREFERRED EMBODIMENTS

The starting 2MA in the above reaction is a compound which can be obtained in good yields from acrylonitrile, 2-methylimidazole and dicyandiamide by the method described in Japanese patent application No. 36391/1972.

The other starting material, epichlorohydrin, is a compound which is produced in quantities as a material for general-purpose epoxy resins.

In one preferred embodiment, a starting mixture composed of 1 mole of 2MA, 1 mole of epichlorohydrin, a small amount (i.e., a catalytic amount) of a polymerization inhibitor such as Na$_2$S9H$_2$O and a suitable amount of water is heated under reflux for 30 minutes with stirring (when heated, the mixture becomes a complete solution, and then crystals begin to precipitate from it).

The resulting reaction mixture is cooled, and the crude product (VT) is collected by filtration. Recrystallization of the crude product in a customary manner gives the final desired product in pure form.

Various commercial polymerization inhibitors, such as hydroquinone and sodium sulfide (Na$_2$S.9H$_2$O), can be used, but the use of sodium sulfide is most economical.

EXAMPLE

A starting material composed of 0.1 mole (21.9 g) of 2MA, 0.1 mole (9.25 g) of epichlorohydrin, a catalytic amount of sodium sulfide (Na$_2$S.9H$_2$O) and 50 ml of water was heated under reflux for 30 minutes with stirring. The resulting reaction mixture was cooled, and 0.1 mole (13.7 g; the yield was quantitative) of the crude product (VT) was collected by filtration. Since the crude product showed a melting point of 237° to 240° C. which is much the same as the melting point of an authentic sample of VT, it was considered to be VT having a considerably high purity.

The crude product was recrystallized from water containing a small amount of sodium sulfide to give 0.076 mole (10.4 g; yield based on 2MA 76 mole%) of the purified product. The product had a melting point of 239° to 241° C.

The filtrate left after the recovery of the crude product was neutralized with sodium carbonate. The sodium ion in the neutralized liquid was removed by a sulfonic acid-type ion exchange resin, and then it was concentrated under reduced pressure. The residue was chromatographed on a silica column to give 0.06 mole (9.4 g; yield based on 2MA 60 mole%) of 1-(β,γ-dihydroxy)-propyl-2-methylimidazole.

1-(β,γ-Dihydroxy)propyl-2-methylimidazole had the following properties.

Melting point: >250° C.

Colorless and resinous. Basic.

$\nu_{cm-1}^{KBr}$: 1620 (6th absorption), 1585 (3rd absorption), 1520 (2nd absorption), 1415 (2nd absorption), 1255 (2nd absorption), 1100 (1st absorption), 1025 (5th absorption), 860 (5th absorption), 750 (4th absorption).

NMR (D$_2$O): δ 7.50 (s, 2H(protons at the 4- and 5-positions of imidazole)), 4.34 (m, 5H (propyl group)), 2.72 (s, 3H (methyl group)).

What is claimed is:

1. A process for synthesizing 2-vinyl-4,6-diamino-s-triazine represented by the structural formula

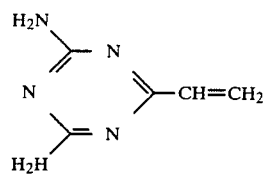

which comprises reaction 2-(2'-methylimidazolyl(1'))-ethyl-4,6-diamino-s-triazine represented by the structural formula

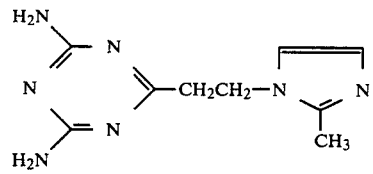

with epichlorohydrin represented by the structural formula

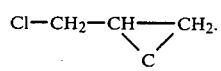

2. The process of claim 1 wherein 2-(2'-methylimidazolyl(1'))-ethyl-4,6-diamino-s-triazine and epichlorohydrin are reacted in substantially equimolar proportions.

3. The process of claim 1 wherein the reaction is carried out in an aqueous medium in the presence of a catalytic amount of a polymerization inhibitor.

4. The process of claim 3 wherein the polymerization inhibitor is sodium sulfide.

5. The process of claim 3 wherein the reaction is carried out by heating the starting compounds under reflux.

6. The process of claim 1 wherein 2-vinyl-4,6-diamino-s-triazine is separated in the form of crystals from the reaction mixture after the reaction.

* * * * *